United States Patent [19]

Kuo et al.

[11] Patent Number: 5,107,003
[45] Date of Patent: Apr. 21, 1992

[54] PREPARATION OF QUINONES BY THE CERIC-CATALYZED OXIDATION OF AROMATIC DIOLS

[75] Inventors: Yeong-Jen Kuo; Michael Bellas; Phillip M. Hudnall, all of Kingsport, Tenn.

[73] Assignee: Eastman Kodak Company, Rochester, N.Y.

[21] Appl. No.: 670,662

[22] Filed: Mar. 18, 1990

[51] Int. Cl.$^5$ .................. C07C 50/02; C07C 50/04
[52] U.S. Cl. ..................... 552/293; 552/308; 552/309
[58] Field of Search ............ 552/293, 296, 299, 308, 552/309

[56] References Cited

U.S. PATENT DOCUMENTS 4,208,339  6/1980  Costantini et al. ............... 552/293
4,536,337  8/1985  Komatsu et al. ................. 552/296

FOREIGN PATENT DOCUMENTS 3834239  4/1989  Fed. Rep. of Germany ...... 552/293

OTHER PUBLICATIONS

H. Firouzabadi and N. Iranpoor, Synthetic Communications 14, 875.
A. E. Gekhman et al., Kinet. Katal. 30, 362 (1989).

Primary Examiner—C. Warren Ivy
Assistant Examiner—Raymond Covington
Attorney, Agent, or Firm—J. Frederick Thomsen; William P. Heath, Jr.

[57] ABSTRACT

Disclosed is a process for the preparation of quinones by the catalytic oxidation of aromatic diols with a peroxide in the presence of a catalytic amount of ceric trihydroxyhydroperoxide.

5 Claims, No Drawings

PREPARATION OF QUINONES BY THE CERIC-CATALYZED OXIDATION OF AROMATIC DIOLS

This invention pertains to the preparation of quinones by the catalytic oxidation of aromatic diols. More specifically, this invention pertains to the conversion of aromatic diols to the corresponding quinones by contacting an aromatic diol with a peroxide in the presence of a catalytic amount of ceric trihydroxyhydroperoxide.

Quinones such as p benzoquinone, methyl p-benzoquinone, cyclohexyl p benzoquinone, phenyl p-benzoquinone, o-benzoquinone, 1,4 naphthoquinone and the like are valuable chemical intermediates useful in the preparation of herbicides, dyes, photographic initiators and the like. p Benzoquinone also is useful as an inhibitor in processing certain vinyl monomers such as acrylic acid and as a dehydrogenation agent.

Known processes for the manufacture of p-benzoquinone include the oxidation of aniline in the presence of water, sulfuric acid and manganese dioxide. Most of the p-benzoquinone obtained from this process was converted to hydroquinone. U.S. Pat. No. 4,208,339 describes the preparation of p benzoquinone by the oxidation of phenol with oxygen or an oxygen containing gas in the presence of cuprous or cupric ions and a second metal such as nickel, iron, tin, cobalt, chromium, molybdenum or magnesium.

Most of the hydroquinone presently manufactured on a commercial scale does not produce p benzoquinone as an intermediate. Therefore, the primary objective of the present invention is the preparation of quinones from the corresponding aromatic diols in general and the preparation of p benzoquinone from hydroquinone (1,4-benzenediol) in particular.

H. Firouzabadi and N. Iranpoor, Synthetic Communications 14, 875 (1984) describe the preparation of benzoquinone compounds by the oxidation of a benzene solution of benzenediols such as hydroquinone and catechol using ceric trihydroxyhydroperoxide [Ce(OH)$_3$OOH] as the oxidizing agent. This non catalytic process does not employ either air or a peroxide but uses two moles of the oxidizing agent per mole of the reactant. A. E. Gekhman et al., Kinet. Katal. 30, 362 (1989) disclose the oxidation of hydroquinone to p-benzoquinone using oxygen or an oxygen containing gas and salts of certain trivalent rare earth metals. The use of trivalent cerium, however, produced quinhydrone rather than p-benzoquinone.

We have discovered that quinone compounds may be prepared in good yields by contacting an aromatic diol with a peroxide in the presence of a catalytic amount of ceric trihydroxyhydroperoxide and an inert liquid. The aromatic diols which may be used in the process provided by the present invention include unsubstituted and substituted benzenediols, naphthalenediols, anthracenediols and the like. Examples of the substituents which may be present on the substituted benzenediols and naphthalenediols include alkyl of up to about 12 carbon atoms, halogen such as chloro, cycloalkyl such as cyclohexyl and aryl such as phenyl. In addition to hydroquinone, specific examples of suitable aromatic diol reactants are 1,2 benzenediol, methyl 1,4 benzenediol, cyclohexyl 1,4 benzenediol, phenyl 1,4 benzenediol, and 1,2- and 1,4 naphthalenediol. A preferred group of benzenediol reactants and quinone products have the general formulas

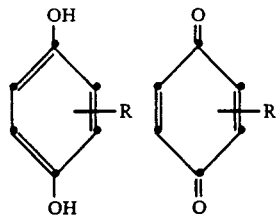

wherein R is hydrogen, alkyl of up to about 8 carbon atoms, halogen, cyclohexyl or phenyl.

Examples of the peroxides which may be used in our novel process include hydrogen peroxide; aliphatic peroxides such as alkyl hydroperoxides, e.g., tertiarybutyl hydroperoxide; peracids such as percarboxylic acids, i.e., a carboxylic acid peroxide, e.g., peracetic acid, perbutyric acid and perbenzoic acid; and the like. Hydrogen peroxide and peracetic acid are the preferred peroxides. The hydrogen peroxide suitable for use in the process comprises aqueous hydrogen peroxide having a peroxide content of 3 to about 90 weight percent. For economic and safety reasons, the aqueous hydrogen peroxide most suitable for use in the process has a hydrogen peroxide content of about 30 to 70 weight percent. It is well known to those skilled in the art that peracetic acid may be generated in situ by several processes, the most important of which comprise the dissolution of hydrogen peroxide in acetic acid or acetic anhydride and the interaction of oxygen with acetaldehyde. These methods of in situ generation of the peroxide are within the scope of our invention. A particularly useful source of peracetic acid is the epoxidation process described by J. T. Lutz, Jr. in Kirk-Othmer, Encyclopedia of Chemical Technology, 3rd Ed., Vol. 9, p. 225-258 (1980). In the epoxidation process, peracetic acid is generated by contacting acetic acid with hydrogen peroxide in the presence of an acidic ion exchange resin.

The amount of peroxide employed in the process of the present invention can vary from 0.75 to 3.0 moles peroxide per mole of aromatic diol reactant. However, the best results are achieved by using about 0.95 to 1. moles peroxide per mole of diol reactant.

The oxidation process provided by the present invention is carried out in an inert solvent such as lower (containing up to about 4 carbon atoms) aliphatic carboxylic acids, e.g., acetic acid; mixtures of lower aliphatic carboxylic acids and water; mixtures of lower aliphatic carboxylic acids and alkanols, e.g., acetic acid and an alkanol having up to about 10 carbon atoms; mixtures of a lower carboxylic acid with hydrocarbons and halogenated hydrocarbons, e.g., mixtures of acetic acid with toluene, benzene, xylenes, chlorobenzene and dichlorobenzenes; mixtures of hydrocarbons and acetone; lower alkyl and aryl esters of aliphatic carboxylic acids, e.g., methyl acetate, ethyl acetate, butyl acetate, phenyl acetate, ethyl propionate and isobutyl isobutyrate; and lower alkyl esters of aliphatic and aromatic dicarboxylic acids, e.g., dimethyl phthalate, diethyl phthalate; and the like. Acetic acid and mixtures of acetic acid and toluene, acetic acid and dimethyl phthalate, and acetic acid and 2 ethylhexanol represent the preferred solvents. Normally, the amount of solvent employed gives a solvent:aromatic diol reactant weight ratio of about 5:1 to 20:1.

The ceric trihydroxyhydroperoxide catalyst is insoluble in the inert solvent and thus the oxidation reaction occurs in a heterogeneous system. The amount of the cerium catalyst employed can be varied widely, e.g., catalytic amounts ranging from about 0.01 to 0.5 mole of ceric trihydroxyhydroperoxide per mole of aromatic diol reactant. The catalyst preferably is employed in an amount which gives a catalyst:diol reactant mole ratio of about 0.15:1 to 0.20:1.

The process may be practiced at a temperature of about 0 to 80° C. although the use of temperatures in the upper portion of this range tends to cause some quinone degradation. The preferred temperature range is about 15° to 40° C. Reaction times of about 30 to 120 minutes normally give good results, e.g., quinone product yields of about 60 to 98% based on the aromatic diol reactant. The quinone product may be isolated according to conventional procedures such as by extraction, filtration, distillation, sublimation and the like.

The process of the present invention may be carried out in a batch, semi continuous or continuous manner. In continuous operation of the process, a solution of the diol reactant in a mixture of fresh and recycled solvent and a peroxide may be fed to a reaction zone comprising one or more agitated reaction vessels containing the ceric trihydroxyhydroperoxide catalyst and maintained at the appropriate reaction temperature. An effluent comprising a solution of the quinone product in the solvent is removed continuously from the reaction zone by means of a filter leg and is fed to a product recovery zone wherein solvent is distilled from the product-containing stream to produce a slurry of the product. The product then is separated from the slurry by filtration and the solvent is recovered and returned to the reaction zone.

A particularly preferred embodiment of the process provided by the present invention concerns the preparation of p benzoquinone by contacting a solution of hydroquinone in an inert solvent with aqueous hydrogen peroxide or peracetic acid and ceric trihydroxyhydroperoxide catalyst at a temperature of about 15° to 40° C.

The operation of our novel process is further illustrated by the following examples wherein GLC refers to gas/liquid chromatography.

EXAMPLE 1

Into a 50 mL, round bottom flask fitted with a dropping funnel and a magnetic stirrer are placed 20 mL of toluene, 0.45 g (0.002 mole) of ceric trihydroxy hydroperoxide catalyst, and 1.1 g (0.01 mole) of hydroquinone. A total of 4 mL of 30% aqueous hydrogen peroxide (0.04 moles $H_2O_2$) is added dropwise and the reaction mixture is stirred at 25° C. for 1 hour. The reaction mixture then is filtered to remove catalyst residues and the organic portion is washed with water 3 times. Analysis of the toluene layer by GLC shows that the yield of p benzoquinone is 94%.

EXAMPLE 2

A 500 mL flask fitted with a mechanical stirrer is charged with 200 mL of acetic acid, 4.5 g (0.02 mole) of ceric trihydroxyhydroperoxide, and 11 g (0.1 mole) of hydroquinone. The flask is immersed in a water bath to maintain a constant temperature. The reaction solution is agitated with a mechanical stirrer at 25° C. for 5–10 minutes and then 40 mL of 30% aqueous hydrogen peroxide (0.4 mole $H_2O_2$) is added dropwise to the solution with stirring. Total reaction time at 25° C. is 1 hour. At the completion of the reaction, 200 mL of isobutyl acetate is added and the mixture is filtered to remove catalyst residues. The filtrate is washed 3 times with water and the solvent is removed by distillation. The crude p-benzoquinone thus obtained (yield =90.2% of theory) is purified by sublimation to give yellow crystals melting at 113.4° C. Similar results are achieved by using toluene or dimethyl phthalate, rather than isobutyl acetate, as the extraction solvent.

EXAMPLE 3

Into a 50 mL, round bottom flask fitted with a dropping funnel and a magnetic stirrer are placed 40 mL of toluene, 10 mL of acetic acid, 0.9 g (0.004 mole) of ceric trihydroxyhydroperoxide, and 2.9 g (0.02 mole) of chlorohydroquinone. A total of 6.6 g of 30% aqueous hydrogen peroxide (0.058 mole $H_2O_2$) is added dropwise to the reaction mixture with stirring and the reaction is continued at 25° C. for 1 hour. The reaction mixture is filtered to remove catalyst residues and the toluene phase is analyzed by GLC which shows that the yield of chloro-p-benzoquinone is 83%.

EXAMPLE 4

The procedure described in Example 3 is repeated using 2.5 g (0.02 mole) of methylhydroquinone as the aromatic diol reactant. The yield of methyl-p-benzoquinone obtained is 79%.

EXAMPLE 5

The procedure described in Example 3 is repeated using 3.3 g (0.02 mole) of tertiary butylhydroquinone as the aromatic diol reactant. The yield of tertiary butyl-p-benzoquinone obtained is 87%.

EXAMPLE 6

The procedure described in Example 3 is repeated using 3.8 g (0.02 mole) of phenylhydroquinone as the aromatic diol reactant and 10 mL toluene and 40 mL acetic acid as the solvent. The yield of phenyl-p-benzoquinone obtained is 60%.

The invention has been described in detail with particular reference to preferred embodiments thereof, but it will be understood that variations and modifications may be effected within the spirit and scope of the invention.

We claim:

1. Process for the preparation of a quinone compound which comprises contacting an aromatic diol with a peroxide in the presence of an inert solvent and a catalytic amount of ceric trihydroxyhydroperoxide.

2. Process according to claim 1 wherein an aromatic diol is contacted with a peroxide selected from hydrogen peroxide and peracetic acid in the presence of an inert solvent and a catalytic amount of ceric trihydroxyhydroperoxide at a temperature of about 15° to 40° C. and wherein the mole ratio of the ceric trihydroxyhydroperoxide:aromatic diol is about 0.15:1 to 0.20:1.

3. Process for the preparation of a quinone compound having the formula which comprises contacting an aromatic diol having the formula

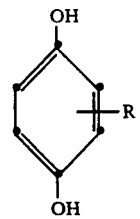

with a peroxide selected from hydrogen peroxide and peracetic acid in the presence of a catalytic amount of ceric trihydroxyhydroperoxide and an inert solvent at a temperature of about 15° to 40° C., wherein the mole ratio of catalyst to aromatic diol is about 0.15:1 to 0.20:1 and R is hydrogen, alkyl of up to about 8 carbon atoms, halogen, cyclohexyl or phenyl.

4. Process for the preparation of p-benzoquinone which catalytic amount of ceric trihydroxyhydroperoxide in an. inert solvent with aqueous hydrogen peroxide or peracetic acid at a temperature of about 15° to 40° C.

5. Process according to claim 4 for the preparation of p-benzoquinone which comprises contacting a solution of hydroquinone in an inert solvent selected from toluene, acetic acid or a mixture thereof with aqueous hydrogen peroxide or peracetic acid at a temperature of about 15° to 40° C., wherein the mole ratio of ceric trihydroxyhydroperoxide to aromatic diol is about 0.15:1 to 0.20:1.

* * * * *

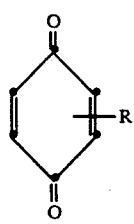

UNITED STATES PATENT AND TRADEMARK OFFICE
CERTIFICATE OF CORRECTION

PATENT NO.   :   5,107,003
DATED        :   April 21, 1992
INVENTOR(S)  :   Yeong-Jen Kuo et al.

It is certified that error appears in the above-identified patent and that said Letters Patent is hereby corrected as shown below:

Column 6, line 19 (Claim 4, line 2), between "which" and "catalytic", ---comprises contacting a solution of hydroquinone and a--- should be inserted.

Signed and Sealed this

Fifteenth Day of June, 1993

Attest:

MICHAEL K. KIRK

Attesting Officer

Acting Commissioner of Patents and Trademarks